United States Patent [19]

Roesler

[11] Patent Number: 5,847,195

[45] Date of Patent: Dec. 8, 1998

[54] PROCESS FOR THE PRODUCTION OF COMPOUNDS CONTAINING ASPARTATE AND ALDIMINE GROUPS

[75] Inventor: Richard R. Roesler, Wexford, Pa.

[73] Assignee: Bayer Corporation, Pittsburgh, Pa.

[21] Appl. No.: 33,259

[22] Filed: Mar. 2, 1998

[51] Int. Cl.$^6$ .................................................. C07C 229/000
[52] U.S. Cl. ........................... 560/35; 560/118; 560/125; 560/168; 544/200
[58] Field of Search .............................. 560/35, 118, 125, 560/168; 544/200

[56] References Cited

U.S. PATENT DOCUMENTS 5,489,704  2/1996  Squiller et al. .......................... 560/35

*Primary Examiner*—Samuel Barts
*Attorney, Agent, or Firm*—Joseph C. Gil; Thomas W. Roy

[57] ABSTRACT

The present invention relates to a process for preparing compounds containing aspartate and aldimine groups corresponding to the formula

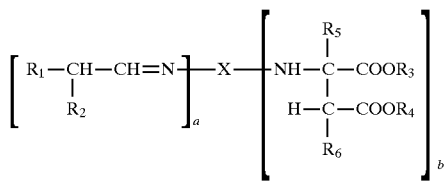

by a) reacting 50 to 95 mole % of the primary amino groups present in a polyamine containing 2 to 6 primary amino groups with a maleic or fumaric acid ester until at least 98% of the unsaturated groups have reacted and b) subsequently reacting the remaining primary amino groups with an aldehyde.

12 Claims, No Drawings

PROCESS FOR THE PRODUCTION OF COMPOUNDS CONTAINING ASPARTATE AND ALDIMINE GROUPS

BACKGROUND OF THE INVENTION

1. Field of the Invention

The present invention relates to an improved process for the preparation of compounds containing aldimine and aspartate groups, which are storage stable.

2. Description of the Prior Art

Compounds containing aspartate groups and aldimine groups are known and described in U.S. Pat. No. 5,489,704. One of the advantages of these compounds is their reduced reactivity in comparison to primary amines. While it is possible to use mixtures of compounds containing aspartate groups and compounds containing aldimine groups, compounds containing both of these group are advantageous because each of these groups are often used in coating compositions to obtain synergistic properties in the cured film.

In addition, it is difficult to prepare the polyaspartates, which are free from starting primary amine, because the Michael addition reaction between maleate esters and primary amines is difficult to complete. This difficulty is not present during the production of compounds containing aspartate groups and aldimine groups because any primary amino groups present after aspartate-forming reaction are converted to aldimine groups in a subsequent step.

One of the disadvantages of the compounds containing aspartate and aldimine groups according to U.S. Pat. No. 5,489,704 is that some of these products do not remain stable in storage, i.e., they undergo an increase in viscosity.

Accordingly, it is an object of the present invention to provide compounds containing aspartate and aldimine groups, which do not suffer from the problem of viscosity increases during storage and which possess the other valuable properties of these compounds.

This object may be achieved with the improved process according to the invention which is described in more detail hereinafter.

SUMMARY OF THE INVENTION

The present invention relates to a process for preparing compounds containing aspartate and aldimine groups corresponding to the formula

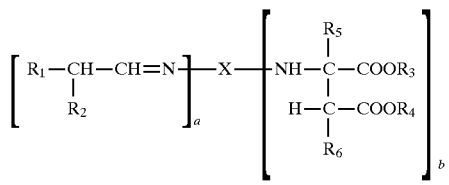

by a) reacting 50 to 95 mole % of the primary amino groups present in a polyamine containing 2 to 6 primary amino groups with a maleic or fumaric acid ester corresponding to the formula

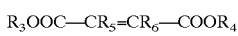

until at least 98% of the unsaturated groups have reacted and b) subsequently reacting the remaining primary amino groups with an aldehyde corresponding to the formula

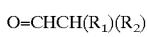

wherein

X represents an organic group which has a valency of n and is inert towards isocyanate groups at a temperature of 100° C. or less, $R_1$ and $R_2$ may be the same or different and represent optionally substituted hydrocarbon radicals, or $R_1$ and $R_2$ together with the β-carbon atom form a cycloaliphatic or heterocyclic ring and $R_3$ and $R_4$ may be identical or different and represent organic groups which are inert towards isocyanate groups at a temperature of 1000° C. or less and $R_5$ and $R_6$ may be identical or different and represent hydrogen or organic groups which are inert towards isocyanate groups at a temperature of 100° C. or less and a and b represent integers having a value of 1 to 5, provided that the sum of a and b is 2 to 6.

DETAILED DESCRIPTION OF THE INVENTION

In accordance with the present invention it has been discovered that the viscosity increase is due to the reaction of unreacted maleic or fumaric acid esters. It is believed that these esters react with aldimines via an "ene" reaction to form an enamine. An example of this reaction mechanism is the reaction of the aldimine of isobutyraldehyde and a primary monoamine with diethyl fumarate:

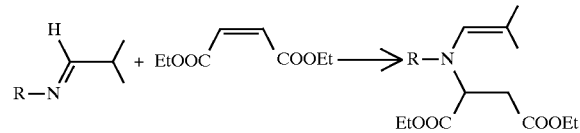

Each of the amine hydrogens of the aldimine can react according to the preceding reaction scheme.

It is critical in accordance with the present invention to ensure that the reaction between the primary amino groups and the maleic or fumaric acid esters is complete before the addition of the aldehyde. This can be done by measuring the content of unsaturated groups, e.g., by iodine titration. This provides the milligrams of maleic acid per gram of resin, which can be used to determine the mole percent of unsaturated groups that remain unreacted. The content of unsaturated groups should be less than 5 mole percent, preferably less than 2 mole percent and more preferably 0 mole percent, before the addition of the aldehyde.

The compounds containing aspartate and aldimine groups that are obtained by the process of the present invention are those corresponding to the formula

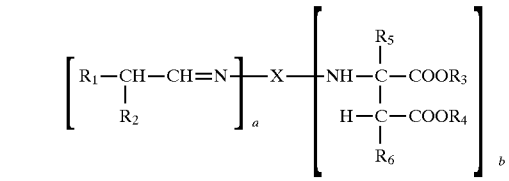

wherein x represents an organic group which has a valency of n and is inert towards isocyanate groups at a temperature of 100° C. or less, preferably a hydrocarbon group obtained by the removal of the amino groups from an aliphatic, araliphatic or cycloaliphatic polyamine, more preferably a diamine, $R_1$ and $R_2$ may be the same or different and represent optionally substituted hydrocarbon radicals, preferably containing 1 to 10, more preferably 1 to 6, carbon atoms, or $R_1$ and $R_2$ together with the β-carbon atom form a cycloaliphatic or heterocyclic ring, $R_3$ and $R_4$ may be identical or different and represent organic groups which are inert towards isocyanate groups at a temperature of 100° or less, preferably methyl or ethyl groups, $R_5$ and $R_6$ may be identical or different and represent hydrogen or organic groups which are inert towards isocyanate groups at a temperature of 100° C. or less, preferably hydrogen, and a and b represent integers with a value of 1 to 5, preferably 1 to 3 and more preferably 1, provided that the sum of a and b is 2 to 6, preferably 2 to 4 and more preferably 2.

The compounds containing aspartate and aldimine groups are prepared by reacting polyamines with maleic or fumaric acid esters and subsequently aldehydes. Suitable polyamines are those corresponding to the formula

wherein

X is as previously defined and n represent an integer having a value of 2 to 6, preferably 2 to 4 and more preferably 2.

The polyamines include high molecular weight amines having molecular weights of 400 to about 10,000, preferably 800 to about 6,000, and low molecular weight amines having molecular weights below 400. The molecular weights are number average molecular weights ($M_n$) and are determined by end group analysis (NH number). Examples of these polyamines are those wherein the amino groups are attached to aliphatic, cycloaliphatic, araliphatic and/or aromatic carbon atoms.

Suitable low molecular polyamine starting compounds include ethylene diamine, 1,2- and 1,3-propane diamine, 2-methyl-1,2-propane diamine, 2,2-dimethyl-1,3-propane diamine, 1,3- and 1,4-butane diamine, 1,3- and 1,5-pentane diamine, 2-methyl-1,5-pentane diamine, 1,6-hexane diamine, 2,5-dimethyl-2,5-hexane diamine, 2,2,4-and/or 2,4,4-trimethyl-1,6-hexane diamine, 1,7-heptane diamine, 1,8-octane diamine, 1,9-nonane, diamine, 1,10-decane diamine, 1,11-undecane diamine, 1,12-dodecane diamine, 1-amino-3-aminomethyl-3,5,5-trimethyl cyclohexane, 2,4- and/or 2,6-hexahydrotoluylene diamine, 2,4'- and/or 4,4'-diamino-dicyclohexylmethane, 3,3'-dialkyl-4,4'-diamino-dicyclohexyl methanes (such as 3,3'-dimethyl-4,4'-diamino-dicyclohexyl methane and 3,3'-diethyl-4,4'-diamino-diamino-dicyclohexyl methane), 1,3- and/or 1,4-cyclohexane diamine, 1,3-bis(methylamino)-cyclohexane, 1,8-p-menthane diamine, hydrazine, hydrazides of semicarbazido carboxylic acids, bis-hydrazides, bis-semicarbazides, phenylene diamine, 2,4- and 2,6-toluylene diamine, 2,3-and 3,4-toluylene diamine, 2,4'- and/or 4,4'-diaminodiphenyl methane, higher functional polyphenylene polymethylene polyamines obtained by the aniline/formaldehyde condensation reaction, N,N,N-tris-(2-amino-ethyl) -amine, guanidine, melamine, N-(2-aminoethyl)-1,3-propane diamine, 3,3'-diamino-benzidine, polyoxypropylene amines, polyoxy-ethylene amines, 2,4-bis-(4'-aminobenzyl)-aniline and mixtures thereof.

Preferred polyamines are 1-amino-3-aminomethyl-3,5,5-trimethyl-cyclohexane (isophorone diamine or IPDA), bis-(4-aminocyclo-hexyl)-methane, bis-(4-amino-3-methylcyclohexyl)-methane, 1,6-diamine-hexane, 2-methyl pentamethylene diamine and ethylene diamine.

Suitable high molecular weight polyamines correspond to the polyhydroxyl compounds known from polyurethane chemistry with the exception that the terminal hydroxy groups are converted to amino groups, either by amination or by reacting the hydroxy groups with a diisocyanate and subsequently hydrolyzing the terminal isocyanate group to an amino group.

Examples of the high molecular weight compounds are polyester polyols, polyether polyols, polyhydroxy polycarbonates, polyhydroxy polyacetals, polyhydroxy polyacrylates, polyhydroxy polyester amides and polyhydroxy polythioethers. The polyester polyols, polyether polyols and polyhydroxy polycarbonates are preferred. Further details concerning suitable starting materials and methods for preparing the high molecular weight polyhydroxy compounds are disclosed in U.S. Pat. No. 4,701,480, herein incorporated by reference.

Preferred high molecular weight polyamines are amine-terminated polyethers, such as the Jeffamine resins available from Texaco.

Suitable optionally substituted maleic or fumaric acid esters for use in the preparation of the compounds containing aspartate and aldimine groups are those corresponding to the formula

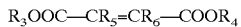

wherein $R_3$, $R_4$, $R_5$ and $R_6$ are as previously defined. Examples include the dimethyl, diethyl and di-n-butyl esters of maleic acid and fumaric acid and the corresponding maleic or fumaric acid esters substituted by methyl in the 2- and/or 3-position. Also suitable are the corresponding mixed alkyl esters of the preceding acids, such as methyl n-propyl maleate.

Suitable aldehydes for use in preparing the compounds containing aspartate and aldimine groups are those corresponding to the formula

wherein $R_1$ and $R_2$ are as previously defined.

Examples include isobutyraldehyde, 2-ethyl hexanal, 2-methyl butyraldehyde, 2-ethyl butyraldehyde, 2-methyl valeraldehyde, 2,3-dimethyl valeraldehyde, 2-methyl undecanal and cyclohexane carboxyaldehyde.

The preparation of compounds containing aspartate and aldimine groups b) takes place by reacting the polyamines with the maleic or fumaric acid esters and subsequently with the aldehydes at a temperature of 0° to 100° C. Excess starting materials and the water which is produced by the aldehyde/amine condensation reaction may be removed by distillation after the reaction. The reaction may be carried out solvent-free or in the presence of suitable solvents such as methanol, ethanol, propanol, dioxane and mixtures of such solvents. As previously discussed, it is important to ensure that the amine/unsaturated ester reaction is complete, or at least substantially complete, before the addition of the aldehyde.

In addition the compounds containing aspartate and aldimine groups, the products obtained in accordance with process of the present invention also contain the pure aldimines and the pure aspartates. Higher amounts of the pure aldimines can be obtained by reacting less than 50% of the amino groups of a diamine with a maleic or fumaric acid ester and then reacting the remainder of the amino groups with an aldehyde. The percentage of component c) in the mixture can be theoretically calculated from percentage of amino groups which can react with the maleic or fumaric acid ester. The smaller the percentage of amino groups which react with maleic or fumaric acid ester, the greater the percentage of pure aldimines that will be present in the mixture in combination with the compounds containing aspartate and aldimine groups.

Similarly, higher percentages of pure aspartates can be obtained by reacting more than 50% of the amino groups with the maleic or fumaric acid ester and then reacting the remainder of the amino groups with an aldehyde. The greater the percentage of amino groups which react with maleic or fumaric acid ester, the greater the percentage of pure aspartates which will be present in the mixture in combination with the compounds containing aspartate and aldimine groups.

Generally, the compositions according to the invention contain 15 to 100%, preferably 20 to 80% and more preferably 30 to 70%, by weight of the compounds containing aspartate and aldimine groups; 0 to 75%, preferably 5 to 75% and more preferably 20 to 70%, by weight of pure aldimines; and 0 to 50%, preferably 0 to 40 and more preferably 0 to 30% of pure aspartates.

The compounds containing aspartate and aldimine groups may be blended with polyisocyanates and reacted to form polyisocyanate addition products, e.g., for the production of coatings. Suitable polyisocyanates are disclosed in U.S. Pat. No. 5,489,704 (herein incorporated by reference).

The compounds containing aspartate and aldimine groups are present in an amount sufficient to provide an equivalent ratio of isocyanate groups to aldimine groups and aspartate groups of 0.5:1 to 20:1, preferably 0.8:1 to 3:1 and more preferably 1:1 to 2:1.

The binders to be used according to the invention are prepared by mixing all of the individual components together or by premixing two or more of the components before adding the other components. However, it is preferable to mix the isocyanate-reactive components together and then to blend the resulting mixture with the polyisocyanate component.

Preparation of the binders is carried out solvent-free or in the presence of the solvents conventionally used in polyurethane or polyurea coatings. It is an advantage of the process according to the invention that the quantity of solvent used may be greatly reduced when compared with that required in conventional two-component systems based on polyisocyanates and polyols.

Examples of suitable solvents include xylene, butyl acetate, methyl isobutyl ketone, methoxypropyl acetate, N-methyl pyrrolidone, Solvesso solvent, petroleum hydrocarbons and mixtures of such solvents.

In the coating compositions to be used for the process according to the invention, the ratio by weight of the total quantity of reactive components to the quantity of solvent is about 40:60 to 100:0, preferably about 60:40 to 100:0.

In addition to the reactive components, the coating compositions may also contain the known additives from coatings technology, such as fillers, pigments, softeners, high-boiling liquids, catalysts, UV stabilizers, anti-oxidants, microbiocides, algicides, dehydrators, thixotropic agents, wetting agents, flow enhancers, matting agents, anti-slip agents, aerators and extenders. Coating compositions containing pigments and/or fillers are especially suitable for the present invention due to the difficulty of removing all of the moisture from these additives.

The coating compositions according to the invention have good storage stability and provide coatings which have relatively fast dry times. The coatings are also characterized by high hardness, elasticity, very good resistance to chemicals, high gloss, good weather resistance, good environmental etch resistance and good pigmenting qualities.

The invention is further illustrated, but is not intended to be limited by the following examples in which all parts and percentages are by weight unless otherwise specified.

EXAMPLES

General procedure for the preparation of compounds containing aldimine and aspartate groups 2 equivalents (1 mole) of the diamine starting material were charged at ambient temperature to a two liter, three necked flask equipped with a stirrer, nitrogen inlet, thermocouple and a 25° C. water bath. 1 equivalent (1.6 equivalents in Example 5 and 1.8 equivalents in Example 6) of diethyl maleate was then added dropwise with stirring at a rate such that the reaction exotherm did not increase the temperature of the reaction mixture above 25° C. (approximately 2 hours). When the addition was complete, the contents of the reaction flask were maintained at 60° C. After 2 to 3 hours the unsaturation number was determined by iodine titration. (In Examples 5 and 6 the unsaturation number was determined daily.) When the unsaturation number was 0, the reaction mixture was cooled to 25° C. 1.2 equivalents (0.48 equivalents in Example 5 and 0.24 equivalents in Example 6) of isobutyraldehyde were then added dropwise to the reaction mixture over a 1 hour period. The reaction exotherm raised the temperature of the mixture to about 400° C. After the addition was complete, the temperature of the reaction mixture was increased to 600° C. and maintained at that temperature for 5 hours. Water and excess isobutyraldehyde were removed by azeotropic distillation, followed by a vacuum distillation (ca. 1 torr) to remove trace quantities of isobutyraldehyde. The resulting product was a low viscosity liquid.

The following Table sets forth the diamine starting material, the theoretical aspartate/aldimine equivalent ratio and the initial viscosity and the viscosity after storage for 3 months.

| Example | Diamine | Aspartate/ Aldimine Equiv. Ratio | Time to obtain unsat no. of 0 | Viscosity at 25° C. (mPa.s) Initial | 3 Months |
|---|---|---|---|---|---|
| 1 | HMDI[1] | 50:50 | 6 hours | 1020 | 1070 |
| 2 | Dimethyl-HMDI[2] | 50:50 | 8 hours | 480 | 520 |
| 3 | IPDA[3] | 50:50 | 8 hours | 205 | 205 |
| 4 | H$_6$TDI[4] | 50:50 | 8 hours | 64 | 66 |
| 5 | HMDI | 80:20 | 6 days | 1030 | 1050 |
| 6 | HMDI | 90:10 | 7 days | 1040 | 1070 |

[1]-4,4'-diamino-dicyclohexylmethane
[2]-2,2'-dimethyl-4,4'-diamino-dicyclohexylmethane
[3]-1-amino-3-aminomethyl-3,5,5-trimethyl cyclohexane
[4]-a 65/35 mixture of 2,4- and 2,6-hexahydrotoluylene diamine Comparison Example 1

Example 2 was repeated (i.e., dimethyl-HMDI was used as the diamine and the aspartate/aldimine equivalent ratio was 50:50) with the exception that isobutyraldehyde was added 3 hours after the addition of diethyl maleate was complete instead of when the unsaturation number was 0. When isobutyraldehyde was added, the unsaturation number was 3.2, which corresponded to the reaction being 92.4% complete, i.e, 92.4 mole percent of the maleate groups had reacted. Even though most of the maleate groups had reacted, the viscosity of the product was not stable in storage. The initial viscosity of 460 mPa.s increased to 730 mPa.s after storage for ninety days.

The preceding comparison example demonstrates that viscosity stable products are not obtained if minor amounts of unreacted unsaturated groups are present when the aldehyde is added. The examples according to the invention demonstrate that viscosity stable products can be obtained by ensuring that the reaction between the amine and the unsaturated acid ester is substantially complete before the addition of the aldehyde.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a compound containing aspartate and aldimine groups corresponding to the formula

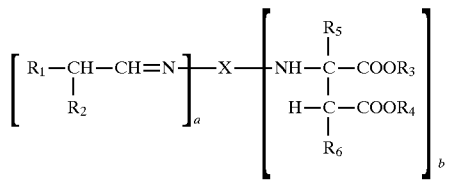

which comprises a) reacting 50 to 95 mole % of the primary amino groups present in a polyamine containing 2 to 6 primary amino groups with a maleic or fumaric acid ester corresponding to the formula $$R_3OOC-CR_5=CR_6-COOR_4$$

until at least 95 mole percent of the unsaturated groups have reacted and b) subsequently reacting the remaining primary amino groups with an aldehyde corresponding to the formula $$O=CHCH(R_1)(R_2)$$

wherein

X represents an organic group which has a valency of n and is inert towards isocyanate groups at a temperature of 100° C. or less, $R_1$ and $R_2$ may be the same or different and represent optionally substituted hydrocarbon radicals, or $R_1$ and $R_2$ together with the β-carbon atom form a cycloaliphatic or heterocyclic ring and $R_3$ and $R_4$ may be identical or different and represent organic groups which are inert towards isocyanate groups at a temperature of 100° C. or less and $R_5$ and $R_6$ may be identical or different and represent hydrogen or organic groups which are inert towards isocyanate groups at a temperature of 100° C. or less and a and b represent integers having a value of 1 to 5, provided that the sum of a and b is 2 to 6.

2. The process of claim 1 wherein $R_1$ and $R_2$ represent hydrocarbon radicals containing I to 6 carbon atoms, $R_3$ and $R_4$ represent a methyl or ethyl group, $R_5$ and $R_6$ represent hydrogen, a is 1 and b is 1.

3. The process of claim 1 wherein $R_1$ represents a methyl group and $R_2$ represents an ethyl group.

4. The process of claim 2 wherein $R_1$ represents a methyl group and $R_2$ represents an ethyl group.

5. The process of claim 1 wherein at least 98 mole percent of the unsaturated groups have reacted before the addition of the aldehyde in step b).

6. The process of claim 5 wherein $R_1$ and $R_2$ represent hydrocarbon radicals containing 1 to 6 carbon atoms, $R_3$ and $R_4$ represent a methyl or ethyl group, $R_5$ and $R_6$ represent hydrogen, a is 1 and b is 1.

7. The process of claim 5 wherein $R_1$ represents a methyl group and $R_2$ represents an ethyl group.

8. The process of claim 6 wherein $R_1$ represents a methyl group and $R_2$ represents an ethyl group.

9. The process of claim I wherein 100 mole percent of the unsaturated groups have reacted before the addition of the aldehyde in step b).

10. The process of claim 9 wherein $R_1$ and $R_2$ represent hydrocarbon radicals containing 1 to 6 carbon atoms, $R_3$ and $R_4$ represent a methyl or ethyl group, $R_1$ and $R_6$ represent hydrogen, a is 1 and b is 1.

11. The process of claim 9 wherein $R_1$ represents a methyl group and $R_2$ represents an ethyl group.

12. The process of claim 10 wherein $R_1$ represents a methyl group and $R_2$ represents an ethyl group.

* * * * *